United States Patent
Sawant et al.

(10) Patent No.: US 11,304,886 B2
(45) Date of Patent: *Apr. 19, 2022

(54) N-ACYL SARCOSINES AS ANTIMICROBIALS FOR PRESERVATION OF HOME AND PERSONAL CARE PRODUCTS

(71) Applicant: GALAXY SURFACTANTS LTD., Navi Mumbai (IN)

(72) Inventors: Bhagyesh Jagannath Sawant, Kalyan (East) (IN); Devyani Ashok Mali, Ambernath (East) (IN); Arpit Wankhade, Sainagar (IN); Nirmal Koshti, Piscataway, NJ (US)

(73) Assignee: GALAXY SURFACTANTS LTD., Navi Mumbai (IN)

( * ) Notice: Subject to any disclaimer, the term of this patent is extended or adjusted under 35 U.S.C. 154(b) by 663 days.

This patent is subject to a terminal disclaimer.

(21) Appl. No.: 15/999,810

(22) PCT Filed: Feb. 13, 2017

(86) PCT No.: PCT/IN2017/050058
§ 371 (c)(1),
(2) Date: Aug. 20, 2018

(87) PCT Pub. No.: WO2017/141266
PCT Pub. Date: Aug. 24, 2017

(65) Prior Publication Data
US 2021/0161786 A1    Jun. 3, 2021

(30) Foreign Application Priority Data
Feb. 20, 2016    (IN) .............................. 201621005953

(51) Int. Cl.
*A61K 8/44*    (2006.01)
*A61Q 19/00*    (2006.01)
(Continued)

(52) U.S. Cl.
CPC ................ *A61K 8/44* (2013.01); *A61K 8/042* (2013.01); *A61K 8/062* (2013.01); *A61Q 19/10* (2013.01);
(Continued)

(58) Field of Classification Search
CPC .......... A61K 8/44; A61K 8/042; A61K 8/062; A61K 2800/524; A61K 2800/74; A61Q 19/10
See application file for complete search history.

(56) References Cited

U.S. PATENT DOCUMENTS

| 5,328,629 A | 7/1994 | Crudden |
| 2004/0096526 A1 | 5/2004 | Jung et al. |

(Continued)

FOREIGN PATENT DOCUMENTS

| WO | WO 99/27902 | 6/1999 |
| WO | WO 2015/136546 | 9/2015 |

OTHER PUBLICATIONS

Lanigan, "Final Report on the Safety Assessment of Cocoyl Sarcosine", International Journal of Toxicology, 20(Suppl. 1): 1-14, 2001. (Year: 2001).*

(Continued)

*Primary Examiner* — Jianfeng Song
(74) *Attorney, Agent, or Firm* — Kramer & Amado, P.C.

(57) ABSTRACT

N-Acyl sarcosines of Formula I, wherein, R=$C_7$ alkyl and $C_{10}$ alkenyl group with terminal double bond, are described as new antimicrobial preservatives for home and personal care products.

(Continued)

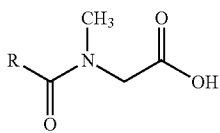

Formula I

Lipidated sarcosines of this patent application preserve creams, lotions, emulsions, solutions or suspensions types of formulations of personal care industry. These are used in: leave-on˜ (cold cream, sunscreen) as well as: rinse-off˜ (facewash, body wash, shampoo) formulations either alone or in combination with other antimicrobials.

1 Claim, 1 Drawing Sheet

(51) Int. Cl.
A61K 8/04 (2006.01)
A61K 8/06 (2006.01)
A61Q 19/10 (2006.01)
(52) U.S. Cl.
CPC .... A61K 2800/524 (2013.01); A61K 2800/74 (2013.01)

(56) References Cited

U.S. PATENT DOCUMENTS

2004/0096528 A1* 5/2004 Miser ................ A61K 8/9789
424/773
2014/0309302 A1* 10/2014 Koshti ................ A61Q 19/00
514/551

OTHER PUBLICATIONS

International Search Report for PCT/IN2017/050058 dated Jun. 1, 2017.
Badreshia, et al., "Iodopropynyl Butylcarbamate", American Journal of Contact Dermatitis, vol. 13, No. 2 (Jun. 2002) pp. 77-79.
Bertelsen, et al., "Triclosan exposure and allergic sensitization in Norwegian children", Allergy, 68 (2013) 84-91.
Degroot, et al., "Isothiazolinone Preservative: Cause of a Continuing Epidemic of Cosmetic Dermatitis", The Lancet (Feb. 11, 1989) pp. 314-.
Du, et al., "In Vitro Neurotoxicity of Methylisothiazolinone, a Commonly Used Industrial and Household Biocide, Proceeds via a Zinc and Extracellular Signal-Regulated Kinase Mitogen-Activated Protein Kinase-Dependent Pathway", The Journal of Neurosciences, 22 (17) Sep. 1, 2002: 7406-7416.
Prosperio, et al., "Nonpreservative substances able to inhibit microbial growth in cosmetics", Cosmetics and Toiletries, 1996 (abstr.).
Harvey, et al., "Endocrine Disrupters and Human Health: Could Oestrogenic Chemicals in Body Care Cosmetics Adversely Affect Breast Cancer Incidence in Women?", Journal of Applied Toxicology, 24, 167-176 (2004).
Kang, et al., "Decreased Sperm Number and Motile Activity on the F1 Offspring Maternally Exposed to Butyl p-Hydroxybenzoic Acid (Butyl Paraben)", J. Vet. Med. Sci. 64 (3): 227-235.
Kumar, et al., "Alteration of testicular steroidogenesis and histopathoogy of reproductive system in male rats treated with triclosan", Reproductive Toxicology 27 (2009) 177-185.
Pedersen, et al., "The Preservatives Ethyl-, Propyl- and Butylparaben are Oestrogenic in an in vivo Fish Assay", Pharmacology & Toxicology 2000, 86, 110-113.
Routledge, et al., "Some Alkyl Hydroxy Benzoate Preservatives (Parabens) are Estrogenic", Toxicology and Applied Pharmacology 153, 12-19 (1998) Article No. T0988544.
Zorrilla, et al., "The Effects of Triclosan on Puberty and Thyroid Hormones in Male Wistar Rats", Toxicological Sciences 107(1), 56-64 (2009).

* cited by examiner

N-ACYL SARCOSINES AS ANTIMICROBIALS FOR PRESERVATION OF HOME AND PERSONAL CARE PRODUCTS

FIELD OF THE INVENTION

The present invention relates to N-acyl sarcosines, namely, N-undecylenoyl sarcosine and N-capryloyl sarcosine as antimicrobials for preservation of home and personal care products. The invention also relates to a facile and cost-effective process of manufacturing the two lipidated sarcosines, individually or as homogeneous mixtures.

BACKGROUND AND PRIOR ART OF THE INVENTION

All current antimicrobials considered to be very effective, are involved in serious controversies. For example, parabens are implicated in disrupting endocrine system, ultimately linked to breast cancer [Pharmacology & Toxicology, Vol. 86(3), pp 110-13, March 2000; Toxicology and Applied Pharmacology, Vol. 153(1), pp. 12-19 Nov. 1998; Journal of Veterinary Medical Science, Vol. 64(3), pp. 227-35, March 2002; Journal of Applied Toxicology, 24 (3), pp. 167-176, 2004]. Formaldehyde is classified as Category 3 CMR (carcinogenic, mutagenic and reproductive toxicity) and hence all formaldehyde releasers are under the cloud. This class includes the work-horse preservatives like DMDM hydantoin, diazolidinyl urea, imidazolidinyl urea and Quaternary 15.

Another class of very effective antimicrobials is: isothiazolinones˜. Methyl and chloromethyl isothiazolinones have been used in preservation of personal care products but these are reported to be neurotoxic and skin sensitizers (Journal of Neuroscience 22 (17), pp. 7408-7416, 2002; The Lancet Vol. 333 (8633), pp. 314-316, 1989).

Halogenated molecules have their own share of controversies. For example, there is a big movement against Triclosan, a high production volume ingredient used as a bactericide in personal care products such as toothpaste deodorant and antibacterial soap. It is a phenolic and halogenated molecule and has been implicated in ecotoxicity (algae, dolphins). It is reported to be an endocrine disruptor (thyroid function and reproductive hormones) (Toxicological Sciences, 107 (1), pp. 56-64, 2009; Reproductive Toxicology, 27(2), pp. 177-185, April 2009) and impairs cardiac and skeletal muscles. There is a special concern for children who are at a higher risk of allergies and the immune systems (Allergy, Vol. 68 (1), pp. 84-91, 2013). The greatest concern is that antimicrobial like Triclosan is contributing to the emergence of antibiotic resistance bacteria. The leading home and personal care companies like Johnson and Johnson, Procter and Gamble have removed Triclosan from their products. Reckitt Benckiser removed it from its household cleaning products and is phasing it out from other products too. Iodopropynyl butyl carbamate (IPBC), another halogenated antimicrobial, is a contact allergen (American Journal of contact dermatitis 13(2), pp. 77-79, 2002). Presence of iodine in its molecular structure gets it implicated in Goiter and malfunctioning thyroid gland. Its use in cosmetics is restricted in Japan, and in European Union (EU) it is allowed only up to 0.02% in leave-on products. Similarly, EU permits usage of methyl dibromo glutaronitrile only up to 0.1% and that too, in only rinse-off products. Halogenated (brominated) molecule like Bronopol, very widely used once upon a time, is banned today in countries like Canada for its usage in cosmetics. It is involved in allergic reactions as well as generation of N-nitroso amine that are known to be carcinogenic. The quaternary ammonium compounds (examples are cetyl pyridinium chloride, benzethonium chloride, benzalkonium chloride) exhibit good antimicrobial activity but their utility in personal care industry is limited due to specific incompatibilities with other cosmetic ingredients, particularly with the ingredients of strong anionic nature.

Thus, it is seen that almost all effective work-horse antimicrobial preservatives such as DMDM hydantoin, imidazolidinyl urea and other formaldehyde releasers, parabens, triclosan, methyl isothiazolinone (MIT), chloromethyl isothiazolinone (CIT) iodopropynyl butyl carbamate (IPBC), Bronopol have been mired into controversies arising due to serious toxicity issues to humans and in some cases environment. Hence, personal care industry is looking for an alternative that would be safe to humans and environment and of course, cost effective.

To overcome this problem, recently, Koshti et al. reported synergistic composition of two N-acyl glycines, N-capryloyl glycine and N-undecylenoyl glycine in water and phenoxy ethanol in the form of a microemulsion for preservation of personal care products (PCT/IN2014/000394). Both N-capryloyl glycine and N-undecylenoyl glycine are well-known antimicrobials (Cosmetics & Toiletries, 128, pp. 458-461, 2013; and US20040096526). Commercially both lipidated glycines, N-capryloyl glycine and N-undecylenoyl glycine are available individually from Seppic, France (Lipacide C8G and Lipacide UG respectively) in the form of fine powder. Thus the utility of the lipidated glycines is well-established and currently they are offered as individual separate entities as well as blend of the two in the form of fine powder. The fine powder form of these two lipidated glycines is associated with explosion hazard. Also, recently Koshti et al. proposed (3722/MUM/2015) the manufacturing process for mixture of N-capryloyl glycine and N-undecylenoyl glycine with minimum effluent generation and converting the mix into flake form instead of powder form to avoid dust hazard on large scale manufacture. However, the proposed sustainable manufacture of these lipidated glycines in this patent application involves capital intensive sophisticated wiped film evaporation, under vacuum.

Hence, there is a need in the art to develop novel antimicrobials and a manufacturing process that obviates elaborate manufacturing setup and also generates less amount of effluent.

The inventors of the present patent application have developed novel antimicrobials and the process that meets the above mentioned objectives.

OBJECTS OF THE INVENTION i. In view of the long list of controversial preservatives, it is the objective of the present invention to design an antimicrobial that would be devoid of halogens, phenolic group and formaldehyde releasing moieties.

ii. It is another objective of the present invention to provide an effective antimicrobial that would be safe to humans as well as to the environment.

iii. A further objective of the present invention is to provide a cost-effective, sustainable manufacturing process for the antimicrobial covering the aspects of renewable raw materials, near quantitative conversion/yield with lesser unit operations and minimal effluent generation.

SUMMARY OF INVENTION

Figure 1:
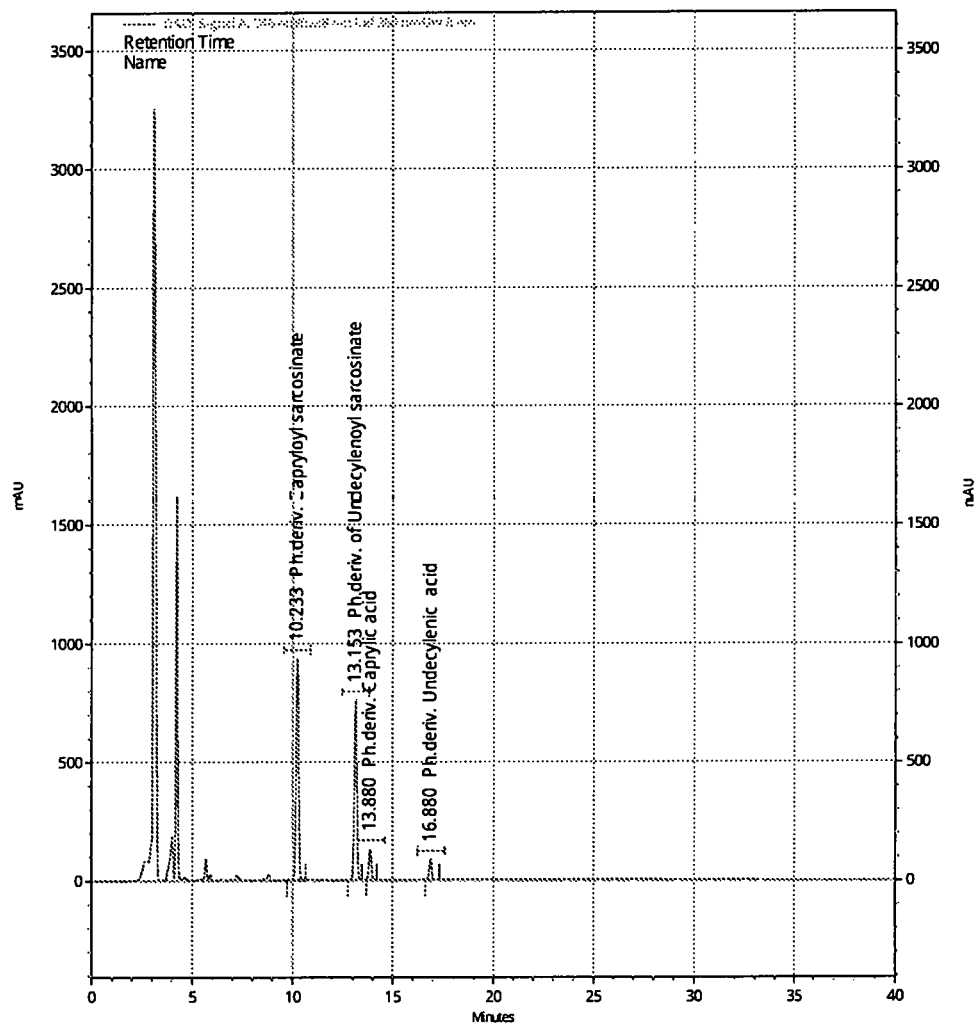
FIG. 1 shows the resolution chromatogram of N-acyl sarcosines from the traces of corresponding fatty acids.

In an aspect, the present patent application provides a safe, sustainable antimicrobial for preservation of personal and home care compositions. The new class of non-hazardous antimicrobials of this patent application is lipidated sarcosines, namely, N-capryloyl sarcosine and N-undecylenoyl sarcosine and the blends thereof (Formula I),

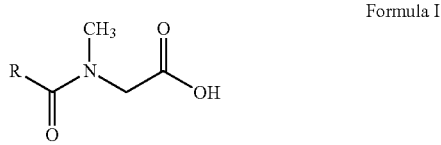

Formula I wherein, R=$C_7$ alkyl and/or $C_{10}$ alkenyl group with terminal double bond In an another aspect, the present invention is directed to personal care compositions such as shampoos, hand wash, body washes, hair conditioners, creams and lotions that are preserved using lipidated sarcosines of Formula I. The minimum concentration of the two lipidated sarcosines when used together is 0.5% by weight of composition.

Accordingly, the invention provides a personal care composition which comprises N-acyl sarcosines of Formula I,

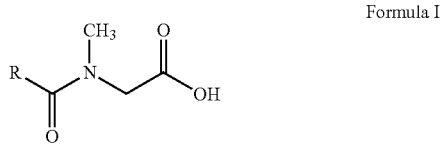

Formula I wherein, R=$C_7$ alkyl and $C_{10}$ alkenyl group with terminal double bond and one or more ingredients selected from the group consisting of surfactants, vegetable oils, petrolatum, mineral oils moisturizers, humectants, rheology modifiers, silicones, cationic conditioners, pearly waxes, emollients, skin actives and hair actives, UV absorbers, film formers, vitamins, solvents, water and antimicrobials listed as preservatives in Cosmetic Directive Annex VI.

The N-acyl sarcosines of Formula I, comprises N-capryloyl sarcosine of formula IV and N-undecylenoyl sarcosine of formula V present together with minimum concentration of 0.5% by weight of the composition.

In a further aspect, the ratio of N-capryloyl sarcosine and N-undecylenoyl sarcosine is 1:1.

In another aspect, the composition according to invention optionally comprises Phenoxy ethanol, as additional antimicrobial.

In yet another aspect the composition according to the invention comprises, a. At least 0.5% w/w N-capryloyl sarcosine and N-undecylenoyl sarcosine;
b. At least 0.5% w/w Phenoxy ethanol.

The above described features, benefits and advantages of the present disclosures will be appreciated and understood by those skilled in the art from the following detailed description and the claims.

DETAILED DESCRIPTION OF INVENTION

In an aspect the present patent application provides a safe, sustainable antimicrobial for preservation of personal and home care compositions comprising the same. The new class of non-hazardous antimicrobials of this patent application is lipidated sarcosines, namely, N-capryloyl sarcosine and N-undecylenoyl sarcosine and the blends thereof (Formula I),

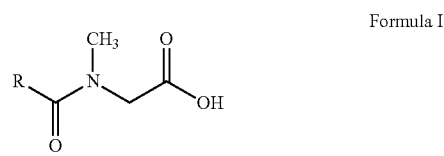

Formula I wherein, R=$C_7$ alkyl and/or $C_1$ alkenyl group with terminal double bond As described in the background section, the personal care industry is looking for safe antimicrobials for preservation. Designing a new, non-toxic (to humans as well as environment) and effective antimicrobial molecule is like looking out for the Biblical: Holy Grail⁻. Another approach to address this situation is to look for existing personal care ingredients that coincidentally possess antimicrobial activity. The literature (WO1999027902, US20040096526) talks about possible use of well-established personal care ingredients like N-capryloyl glycine (II) and N-undecylenoyl glycine (III) as preservatives for home and personal care products.

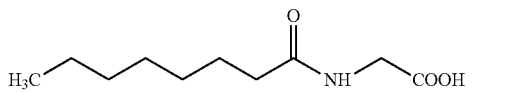

Formula II

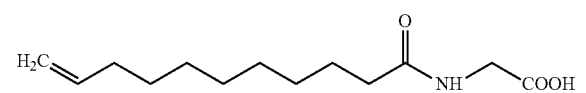

Formula III

The inventors of the present patent application surprisingly discovered that the analogous N-acyl sarcosines, N-capryloyl sarcosine (IV) and N-undecylenoyl sarcosine (V) not only show equivalent antimicrobial activity but they are extremely easy to synthesize on bulk scale. The new class of non-hazardous antimicrobials of this patent application is lipidated sarcosines, namely, N-capryloyl sarcosine (IV) and N-undecylenoyl sarcosine (V) and the blends thereof (Formula I).

N-acyl aminoacid surfactants are prepared by Schotten Baumann reaction, by reacting long chain acyl chloride with the amino acid (such as glycine/sarcosine) in the presence of a base, in aqueous medium. The aqueous alkaline metal salts thus obtained are acidified and N-acyl amino acids are separated from aqueous mass by either filtration or phase separation. In the second step of acidification (Scheme I) with mineral acid, the lipidated glycines precipitate as fine powder.

Scheme-I

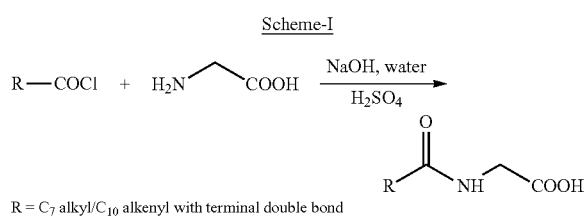

R = C₇ alkyl/C₁₀ alkenyl with terminal double bond

The fine powder of lipoglycines (Formula II & III) thus obtained bind to significant amount of water and simple filtration or centrifugation does not separate the: bound water from the solid particulate lipidated glycines. The wet cake with retained water as high as 30%, needs to be dried by another separate drying operation.

Contrary to the above, isolating the liquid acyl sarcosines (Formula IV and V) of the present invention from acidic aqueous mixture is extremely easy as compared to the solid particles of lipidated glycines (Formula II and III)

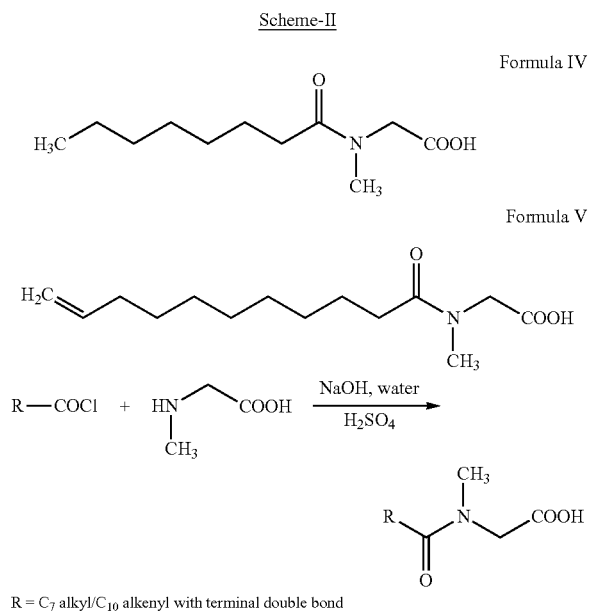

R = C₇ alkyl/C₁₀ alkenyl with terminal double bond

Acyl sarcosines of the present invention do not retain water and hence they are easy to phase separate on acidification. Further, the liquid nature obviates all the problems that are associated with solids (filtration/drying/measures to prevent dust-explosion hazard, material of construction to deal with highly acidic solid material).

This significant difference of retaining water is arising due to NH group of peptide bond in lipidated glycine that is more amenable for hydrogen bonding with water molecules compared to $N(CH_3)$ group of amide linkage of lipidated sarcosines (Formula I). The nitrogen of lipidated sarcosines is fully substituted and methyl group ($N(CH_3)$) can be sterically effective in repelling water. It is also likely that intermolecular hydrogen bonding between two molecules of lipidated amino acids (N-acyl sarcosine and N-acyl glycine) can have a bearing on the amount of water retained while isolating from aqueous medium.

The one pot process to synthesize both lipidated sarcosines is described in Example 3. After performing Schotten Baumann reaction of mixture of fatty acid chlorides (undecylenoyl chloride and capryloyl chloride, in 1:1 weight ratio) with sarcosine in the presence of base, the whole reaction mass is acidified with sulphuric acid to isolate the mixture of the two lipidated sarcosines, N-capryloyl sarcosine and N-undecylenoyl sarcosine in quantitative yield.

Antimicrobial Efficacy of Lipidated Sarcosines:

Formula I

The lipidated sarcosines of Formula I wherein R is $C_7$, alkyl or $C_{10}$, alkenyl chain with double bond at the terminus, exhibit decent antimicrobial activity. The minimum inhibitory concentration (MIC) data for individual N-capryloyl sarcosine and N-undecylenoyl sarcosine and the blend of the two (against Gram positive, Gram negative bacteria and yeast and mold) are given in Table 1. Since both lipidated sarcosines (Formula I) show more or less similar MICs, it is logical to use them in combination so that one can lower the effective concentration of individual N-acyl sarcosine. Combination of two lipidated sarcosines by themselves or in combination with other antimicrobials is useful for discouraging microbes to develop resistance by mutating.

The MIC numbers of lipidated sarcosines are comparable to antimicrobials like N-capryloyl glycine (CAS No. 14246-53-8), N-undecylenoyl glycine (CAS No. 54301-26-7) and well-established antimicrobial such as 2-phenoxy ethanol (Table 2). Phenoxy ethanol is a very popular antimicrobial and personal care industry uses thousands of metric tonnes of the product. It is allowed only up to maximum 1% level in personal care products for adults. However, for babies the allowed limit is far lower.

TABLE 1

Minimum Inhibitory Concentration (MIC) for individual sarcosines, blend of the two sarcosines & blend of two glycines

| Microorganisms | N-Undecylenoyl sarcosine MIC (%) | N-Capryloyl sarcosine MIC (%) | N-Undecylenoyl sarcosine and N-capryloyl sarcosine (1:1) MIC (%) | N-Undecylenoyl glycine and N-capryloyl glycine (1:1) MIC (%) |
|---|---|---|---|---|
| Pseudomonas aeruginosa ATCC 15442 | 0.6 | 0.7 | 0.7 | 0.7 |

TABLE 1-continued

Minimum Inhibitory Concentration (MIC) for individual sarcosines,
blend of the two sarcosines & blend of two glycines

| Microorganisms | N-Undecylenoyl sarcosine MIC (%) | N-Capryloyl sarcosine MIC (%) | N-Undecylenoyl sarcosine and N-capryloyl sarcosine (1:1) MIC (%) | N-Undecylenoyl glycine and N-capryloyl glycine (1:1) MIC (%) |
|---|---|---|---|---|
| *Escherichia coli* ATCC 8739 | 0.7 | 0.7 | 0.7 | 0.6 |
| *Staphylococcus aureus* ATCC 6538 | 0.6 | 0.7 | 0.6 | 0.6 |
| *Propionibacterium acnes* ATCC 1953 | 0.7 | 0.6 | 0.7 | 0.5 |
| *Candida albicans* ATCC 10231 | 0.6 | 0.7 | 0.7 | 0.6 |
| *Aspergillus niger* ATCC 16404 | >1.0 | >1.0 | >1.0 | >1.0 |
| *Malassezia furfur* MTCC 1374 | 0.6 | 0.6 | 0.6 | 0.6 |

Table 2 shows the minimum inhibitory concentration of phenoxy ethanol. It can be seen from the comparative values given in Table 1 that the effective range is quite close to that obtained in 1:1 mixture of N-capryloyl sarcosine and N-undecylenoyl sarcosine. For most microorganisms the minimum inhibitory concentration numbers for both phenoxy ethanol and the blend of two lipidated sarcosines is above 0.5%. Inhibiting growth of the mold *Aspergillus niger* is always a challenge. Individually, both Phenoxy ethanol & 1:1 blend of N-capryloyl and N-undecylenoyl sarcosine show significantly weak activity against this mold. Phenoxy ethanol has minimum inhibitory concentration of 0.9% against *A. niger* (Table 2) whereas blend of the two lipidated sarcosines does not inhibit growth of *A. niger* up to 1.0% (Table 1).

TABLE 2

Minimum Inhibitory Concentration for phenoxy ethanol
A cream formulation (emulsion type which contains around
70% water) fails the challenge test when preserved either with
only 0.5% phenoxy ethanol (Example 5, Table 3)
or with 0.5% of 1:1 w/w blend of N-capryloyl sarcosine and
N-undecylenoyl sarcosine (Example 4).

| Microorganisms | MIC in % |
|---|---|
| *Pseudomonas aeruginosa* ATCC 15442 | 0.8 |
| *Escherichia coli* ATCC 8739 | 0.6 |
| *Staphylococcus aureus* ATCC 6538 | 0.8 |
| *Propionibacterium acnes* ATCC 1953 | 0.4 |
| *Candida albicans* ATCC 10231 | 0.6 |
| *Aspergillus niger* ATCC 16404 | 0.9 |
| *Malassezia furfur* MTCC 1374 | 0.6 |

TABLE 3

Challenge test on cream formulation preserved with
0.5 pheoxy ethanol

| TVC in cfu/gm | *Staphylococcus aureus* ATCC 6538 | *Escherichia coli* ATCC 8739 | *Propionibacterium acnes* MTCC 1951 | *Pseudomonas aeruginosa* ATCC 15442 | *Candida albicans* ATCC 10231 | *Aspergillus niger* ATCC 16404 | *Malassezia furfur* MTCC 1374 |
|---|---|---|---|---|---|---|---|
| 0 day | 2303833.33 | 9955500 | 2572167 | 11972167 | 219000 | 1538833 | 6888833 |
| 24 hrs | 235500 | 1135500 | 46833.33 | 883.3333 | 4316.667 | 107166.7 | 1133833 |
| 48 hrs | 1084500 | 40666.67 | 23500 | 616.6667 | 185 | 805500 | 23516.67 |
| 7 days | 500 | 0 | 0 | 566.6667 | 0 | 72166.67 | 0 |
| 14 days | 0 | 0 | 0 | 0 | 0 | 20666.67 | 0 |

However, interestingly when the same cream formulation (Example 6) is preserved with 0.5% of phenoxy ethanol along with 0.5% of 1:1 blend of N-capryloyl sarcosine and N-undecylenoyl sarcosine, it passes the challenge test very effectively as is evident from MIC values given in Table 4. Thus, the cream formulation employs a concentration that is well below MIC for all microbes. However, when combined together at concentration that is lower than the MIC, the combination works, showing the additive effect that results in broad spectrum of antimicrobial activity. Cream formulation (:leave-on˜) using lipidated sarcosines when used at 1.0% by weight survives the challenge. Similarly, the blend of capryloyl sarcosine and undecylenoyl sarcosine at 1.2% by weight preserves the: rinse-off˜˜ body wash formulation. Similar results of antimicrobial efficacy are obtained when compounds of Formula I were used to preserve the shower gel formulations described in Example 7 and 8. The shower gel formulation when preserved with 1% by weight of 1:1 mixture of capryloyl sarcosine and undecylenoyl sarcosine did not survive the challenge test particularly against *A. niger*. However, the shower gel formulation of Example 8, when preserved with 0.5% lipidated sarcosine along with phenoxy ethanol at 0.5% level, cleared the challenge test for all microbes including, the mold *A. niger*.

genated phenolic derivatives like chloroxylenol, Triclosan & iodopropynyl butyl carbamate; organic acids such as benzoic acid, sorbic acid and their salts; and other suitable alcohols like phenoxy ethanol, caprylyl glycol and 2-ethyl hexyl glycerin.

Thus the present invention provides personal care compositions comprising N-acyl sarcosines of Formula I,

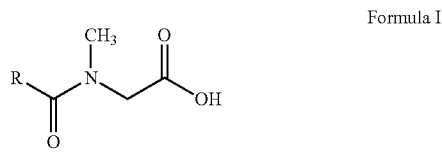

Formula I wherein, R=$C_7$ alkyl and $C_{10}$ alkenyl group with terminal double bond along with one or more ingredients selected from the group consisting of surfactants, vegetable oils, petrolatum, mineral oils moisturizers, humectants, rheology modifiers, silicones, cationic conditioners, pearly waxes, emollients, skin actives and hair actives, UV absorbers, film formers, vitamins, solvents, water and antimicrobials listed as preservatives in Cosmetic Directive Annex VI.

TABLE 4

Challenge test on a cream formulation with 0.5% lipidated sarcosines (undecylenoyl sarcosine: capryloyl sarcosine::1:1) and 0.5% phenoxy ethanol

| TVC in cfu/gm | Staphylococcus aureus ATCC 6538 | Escherichia coli ATCC 8739 | Propionibacterium acnes MTCC 1951 | Pseudomonas aeruginosa ATCC 15442 | Candida albicans ATCC 10231 | Aspergillus niger ATCC 16404 | Malassezia furfur MTCC 1374 |
|---|---|---|---|---|---|---|---|
| 0 day | 500 | 783.3333 | 500 | 55555500 | 1000 | 230500 | 800 |
| 24 hrs | 0 | 0 | 0 | 0 | 0 | 533.3333 | 0 |
| 48 hrs | 0 | 0 | 0 | 0 | 0 | 1870 | 0 |
| 7 days | 0 | 0 | 0 | 0 | 0 | 0 | 0 |
| 14 days | 0 | 0 | 0 | 0 | 0 | 0 | 0 |
| 21 days | 0 | 0 | 0 | 0 | 0 | 0 | 0 |
| 28 days | 0 | 0 | 0 | 0 | 0 | 0 | 0 |

Personal care formulations like creams, lotions, gels, suspensions, emulsions, solutions, dispersions and all water containing formulations can be preserved with the combination of phenoxy ethanol and lipidated sarcosines of the invention. In formulations, the lipidated sarcosines and alcoholic antimicrobials like Phenoxy ethanol do not interact with each other as the concentration at which they are employed as preservative is very less. However, they can˜t be stored together since they do form corresponding esters on standing. This problem of incompatibility can be addressed by creating microemulsion of lipidated sarcosines, water and phenoxy ethanol (Example 9). For preservation of personal care products, N-acyl sarcosines of the present invention can be used with other established antimicrobials synergistically. The other: allowed˜ antimicrobials and their limits are described in Cosmetic Directive Annex VI. It can be easily understood by those who are skilled in the art that various synergistic combinations are possible using the N-acyl sarcosines of the present invention and the antimicrobials that are currently being used. Antimicrobial preservative combinations with both controversial as well as non-controversial antimicrobials are possible. The major categories of antimicrobials that are used for preservation of personal care are parabens; isothiazolinones; halo-

EXAMPLES

The present invention is now described by way of working on non-limiting illustrative examples. The details of the invention provided in the following examples are given by the way of illustration only and should not be construed to limit the scope of the present invention.

Caprylic and undecylenic acids have been procured from Vegetable Vitamin Foods Company (VVF India Ltd).

Example 1: Preparation of N-Undecylenoyl Sarcosine

To a stirred mixture of sarcosine (291 g of 40% aqueous solution, 1.05 gmol) in water (390 g) at 25 éC, undecylenoyl chloride (207 g, 1.0 gmol) and sodium hydroxide solution (83 g of 48% aqueous solution, 1 gmol) are added simultaneously while maintaining temperature between 20 éC to 30 éC and pH between 10.0 to 11.0. The addition takes about two hours. The reaction mass is stirred for additional two hours at 30 éC to 35 éC. The whole reaction mixture is then acidified with sulphuric acid and the aqueous phase containing the inorganic salt is separated from the organic phase. The organic phase is washed again with water to ensure that the organic phase is free from mineral acidity. The isolated organic phase contains N-undecylenoyl sarcosine as colorless liquid (240 g, 94% yield).

Analysis of N-Undecylenoyl Sarcosine:
Acid value=215, Moisture content=<1%
IR (neat, cm$^{-1}$): 1603, 1732, 2854, 2925
$^1$H-NMR (CDCl$_3$): 1.21-1.29 (10H), 1.32-1.56 (2H), 1.93-1.98 (2H), 2.30-2.33 (2H), 2.9-3.1 (3H, two singlets, N-methyl), 3.9-4.0 (2H, methylene of sarcosine, two singlets), 4.83-4.93 (2H), 5.67-5.78 (1H), 9.0 (1H, carboxyl)

Example 2: Preparation of N-Capryloyl Sarcosine

To a stirred mixture of sarcosine (291 g of 40% aqueous solution, 1.05 gmol) in water (320 g) at 25 éC, capryloyl chloride (166 g, 1.0 gmol) and sodium hydroxide solution (83 g of 48% aqueous solution, 1.0 gmol) are added simultaneously while maintaining temperature between 20 éC to 30 éC and pH between 10.0 to 11.0. The addition takes 4 to 5 hours depending on the efficiency of temperature control. The reaction mass is stirred for additional two hours. The whole reaction mixture is then acidified with sulphuric acid and the aqueous phase containing the inorganic salt is separated from the organic phase. The organic phase is washed again with water to ensure that the organic phase is free from mineral acidity. The isolated organic phase is made up of N-capryloyl sarcosine as colorless liquid (200 g, 93% yield).

Analysis of N-Capryloyl Sarcosine:
Acid value=255, Moisture content=<1%
IR (neat, cm): 1602, 1732, 2858, 2926
$^1$H-NMR (CDCl$_3$): 0.78-0.82 (3H), 1.21-1.24 (8H), 1.52-1.56 (2H), 2.17-2.26 (2H), 2.9-3.0 (two singlets, 3H, N-methyl), 3.9 to 4.0 (2H, two singlets for methylene sandwiched between amido and carboxyl group), 10.0 (1H, carboxyl)

Example 3: Preparation of N-Capryloyl Sarcosine and N-Undecylenoyl Sarcosine in Weight Ratio of 1:1

To a stirred mixture of sarcosine (291 g of 40% aqueous solution, 1.05 gmol) in water (350 g) at 25 éC, undecylenoyl chloride (92 g, 0.45 gmol), capryloyl chloride (92 g, 0.55 gmol) and sodium hydroxide solution (83 g of 48% aqueous solution, 1 gmol) simultaneously while maintaining temperature between 20 éC to 30 éC and pH between 10.0 to 11.0. The addition takes about two hours. The reaction mass is stirred for additional two hours at 30 to 35 éC. The whole reaction mixture is then acidified with sulphuric acid and the aqueous phase containing the inorganic salt is separated from the organic phase. The organic phase is washed again with water to ensure that the organic phase is free from mineral acidity. The isolated organic phase is made up of N-undecylenoyl sarcosine and N-capryloyl sarcosine as colorless liquid (220 g, 94% yield).

Analysis of Blend of N-Undecylenoyl Sarcosine and N-Capryloyl Sarcosine:
Acid value: 235, Moisture content <0.66%.
IR (neat, cm$^{-1}$): 1602, 1732, 2858, 2926
Chromatography:
Reversed phase HPLC (C18 column, Acetonitrile-water, UV detection at 245 nm) is performed after converting the sample into UV absorbing phenacyl ester derivatives by reacting lipidated sarcosines and fatty acids with phenacyl bromide (detection at 246 nm) as shown in FIG. 1.

Example 4: Oil/Water Cream: Preservation with the 0.5% of Blend of Example 3

| Components | % (W/W) |
|---|---|
| Phase A | |
| Water | 72.0 |
| Glycerin | 2 |
| Laureth-9 | 0.5 |
| PEG-7 Glyceryl Cocoate | 2 |
| EDTA | 0.05 |
| Phase B | |
| Paraffin Oil | 4 |
| Isopropyl Myristate | 2 |
| Stearic Acid | 7 |
| Glyceryl Monostearate | 6 |
| Cetostearyl Alcohol | 4 |
| Phase C | |
| Undecyneoyl Sarosine and Carpyloyl Sarcosine (Example 3) | 0.5 |
| pH of final formulation = 5 | |

Example 5: Oil/Water Cream: Preservation with 0.5% Phenoxy Ethanol

| Components | % (W/W) |
|---|---|
| Phase A | |
| Water | 71.2 |
| Glycerin | 2 |
| Laureth-9 | 0.5 |
| PEG-7 Glyceryl Cocoate | 2 |
| EDTA | 0.05 |
| Phase B | |
| Paraffin Oil | 4 |
| Isopropyl Myristate | 2 |
| Stearic Acid | 7 |
| Glyceryl Monostearate | 6 |
| Cetostearyl Alcohol | 4 |
| Phase C | |
| Phenoxy ethanol | 0.5 |
| pH of final formulation = 5 | |

Example 6: Oil/Water Cream: Preservation with 0.5% of Blend of Example 3 and 0.5% Phenoxy Ethanol

| Components | % (W/W) |
|---|---|
| Phase A | |
| Water | 72.0 |
| Glycerin | 2 |
| Laureth-9 | 0.5 |
| PEG-7 Glyceryl Cocoate | 2 |
| EDTA | 0.05 |
| Phase B | |
| Paraffin Oil | 4 |
| Isopropyl Myristate | 2 |
| Stearic Acid | 7 |
| Glyceryl Monostearate | 6 |

-continued

| Components | % (W/W) |
|---|---|
| Cetostearyl Alcohol | 4 |
| Phenoxy ethanol | 0.5 |
| Phase C | |
| Undecyneoyl Sarosine and Capryloyl Sarcosine | 0.5 |
| pH of final formulation = 5 | |

Example 7: Shower Gel: Preservation with the 1.0% of Blend of Example 3

| Components | % (W/W) |
|---|---|
| Phase A | |
| Water | 68.6 |
| Sodium Laureth Sulfate (2 EO) | 21.5 |
| Cocamidopropyl Betaine | 6.6 |
| EDTA | 0.1 |
| Phase B | |
| Cocamide MEA | 2 |
| Phase C | |
| Undecyneoyl Sarosine and Carpyloyl Sarcosine | 1.0 |
| pH of final formulation = 5 | |

Example 8: Shower Gel: Preservation with the 0.5% of Blend of Example 3 and 0.5% Phenoxy Ethanol

| Components | % (W/W) |
|---|---|
| Phase A | |
| Water | 68.5 |
| Sodium Laureth Sulfate | 21.5 |
| Cocamidopropyl Betaine | 6.6 |
| EDTA | 0.1 |
| Phase B | |
| Cocamide MEA | 2 |
| Phase C | |
| Undecyneoyl Sarosine and Carpyloyl Sarcosine | 0.5 |
| Phenoxyethanol | 0.5 |
| pH of final formulation = 5 | |

Example 9: Preparation of Microemulsion with Phenoxy Ethanol, N-Capryloyl Sarcosine and N-Undecylenoyl Sarcosine and Water To a stirred suspension of N-undecylenoyl sarcosine and N-capryloyl sarcosine (13 g) from Example 3, in water (33 g) at room temperature, sodium hydroxide flakes (2 g) are added gradually ensuring no increase in the temperature of the reaction mass. To this stirred mass, phenoxy ethanol (52 g) is added and the reaction mass is stirred at room temperature till it becomes homogeneous and transparent

Advantages of the Invention

1) The present invention provides new antimicrobial preservatives, N-acyl sarcosines, namely, N-capryloyl sarcosine and N-undecylenoyl sarcosine and blends thereof, for home and personal care products. This is a significant addition to a depleted reservoir of preservatives for home and personal care industry. The lipidated sarcosines do not contain any halogen (chlorine, bromine, iodine), phenolic moiety as in Triclosan, chlorxylenol, parabens, or hydroxyl methyl like formaldehyde releasing group and hence these are expected to be more safe to human and to the environment N-caployl sarcosine and N-undecylennoyl sarcosine of this present invention provides an option of preserving personal care products by avoiding all the existing controversial antimicrobials.

2) Some of the antimicrobials are controversial due to toxicity and hence their usage is allowed up to certain limit. The dosage of such controversial but allowed antimicrobials can be decreased further in the personal and home care products by using lipidated sarcosines of the present invention along with them.

3) Lipidated sarcosines of the present invention can be used along with the weaker but non-controversial antimicrobials such as N-acyl glycines, sorbic acid, benzoic acid or phenoxy ethanol, benzyl alcohol, 2-ethyl hexyl glycerine, caprylyl glycol to get a broad spectrum of protection against microbes.

4) Lipidated sarcosines of the present invention are equivalent to lipidated glycines in terms of the antibacterial activity but the former are far easy to manufacture and use due to their liquid nature. Relatively, the manufacture of N-acyl sarcosines is surprisingly easy since the isolation of acyl sarcosines from the aqueous acidic reaction mass is extremely facile compared to lipidated glycines which retain huge amount of water due to hydrogen bonding of N—H group of the amide linkage with water molecule.

5) Generation of less amount of effluent and less number of manufacturing steps make the lipidated sarcosines sustainable and safe/eco-friendly, easy to use viable alternative preservatives.

6) Another advantage of the lipidated sarcosines of the present patent application over well-established lipidated glycines is their physical property, in terms of being liquid in nature. Lipidated glycines are solids and the powder form is associated with dust explosion hazard and hence the powder form obtained in the conventional synthesis needs to be converted in the bigger particles by additional operations.

7) The lipidated sarcosines are amenable to economical (lesser unit operations) and sustainable way of manufacture on commercial scale (less effluent generation, no dust prevention measures).

We claim:

1. A composition comprising:
   at least 0.5% w/w of a liquid N-acyl sarcosine of Formula I:

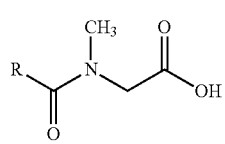

Formula I at least 0.5% w/w phenoxy ethanol; and
   one or more ingredients selected from the group consisting of surfactants, vegetable oils, petrolatum, mineral oils moisturizers, humectants, rheology modifiers, silicones, cationic conditioners, pearly waxes, emollients, skin actives and hair actives, UV absorbers, film formers, vitamins, solvents, water, and antimicrobials;
wherein the liquid N-acyl sarcosine comprises a mixture containing N-capryloyl sarcosine and N-undecylenoyl sarcosine in a ratio of 1:1.

* * * * *